United States Patent
Jirjis et al.

(10) Patent No.: US 9,328,314 B2
(45) Date of Patent: May 3, 2016

(54) METHOD FOR THE PURIFICATION OF LECITHIN

(71) Applicant: Cargill, Incorporated, Wayzata, MN (US)

(72) Inventors: Bassam Farid Jirjis, Plymouth, MN (US); Jeff Molnar, Bellbrook, OH (US); Christoph Schafer, Hamburg (DE); Arnulf Schoeppe, Hamburg (DE)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 14/652,900

(22) PCT Filed: Dec. 16, 2013

(86) PCT No.: PCT/US2013/075289
§ 371 (c)(1),
(2) Date: Jun. 17, 2015

(87) PCT Pub. No.: WO2014/099726
PCT Pub. Date: Jun. 26, 2014

(65) Prior Publication Data
US 2015/0376545 A1    Dec. 31, 2015

Related U.S. Application Data

(60) Provisional application No. 61/739,818, filed on Dec. 20, 2012.

(30) Foreign Application Priority Data

Mar. 13, 2013   (EP) .................................... 13001273

(51) Int. Cl.
| | | |
|---|---|---|
| *C11B 3/00* | (2006.01) |
| *A23J 7/00* | (2006.01) |
| *A23L 1/29* | (2006.01) |
| *C07F 9/10* | (2006.01) |
| *A23K 1/16* | (2006.01) |
| *A23D 9/013* | (2006.01) |
| *A23D 9/04* | (2006.01) |
| *A23L 1/30* | (2006.01) |

(52) U.S. Cl.
CPC ................ *C11B 3/008* (2013.01); *A23D 9/013* (2013.01); *A23D 9/04* (2013.01); *A23J 7/00* (2013.01); *A23K 1/164* (2013.01); *A23L 1/296* (2013.01); *A23L 1/3008* (2013.01); *C07F 9/103* (2013.01); *C11B 3/00* (2013.01); *A23V 2002/00* (2013.01)

(58) Field of Classification Search
CPC ........... C11B 3/008; A23D 9/013; A23D 9/04
USPC ........................................................ 554/83
See application file for complete search history.

(56) References Cited

U.S. PATENT DOCUMENTS 2,013,804 A    9/1935   Klein et al.

FOREIGN PATENT DOCUMENTS

| CN | 1546498 A | 11/2004 |
|---|---|---|
| JP | S5550859 A | 4/1980 |
| JP | S6277394 A | 4/1987 |
| JP | H01197492 A | 8/1989 |
| JP | H05161456 A | 6/1993 |
| JP | H0725888 A | 1/1995 |
| WO | 02/08368 A1 | 1/2002 |

OTHER PUBLICATIONS

THe Vitamin Shoppe's online disclosure of Fearn's Liquid Lecithin.*
International Search Report of International Application No. PCT/US2013/075289 mailed Feb. 4, 2014.

* cited by examiner

*Primary Examiner* — Deborah D Carr

(57) ABSTRACT

A method for the purification of lecithin, comprising the steps of:
  a. reducing the viscosity of lecithin to a viscosity of less than about 10 Pa·s; then
  b. mixing the lecithin with granulated active carbon; then
  c. separating the lecithin from the granulated active carbon and recover purified lecithin.

Lecithin substantially free of poly-aromatic hydrocarbons, and a food or feed product comprising said lecithin.

12 Claims, No Drawings

METHOD FOR THE PURIFICATION OF LECITHIN

CROSS-REFERENCE TO RELATED APPLICATIONS

This application is a national phase application of International Application No. PCT/US2013/075289, filed Dec. 16, 2013, entitled METHOD FOR THE PURIFICATION OF LECITHIN, which claims the benefit of the U.S. patent application Ser. No. 61/739,818 filed Dec. 20, 2012, entitled METHOD FOR THE PURIFICATION OF LECITHIN and European Patent Application Ser. No. 13001273.5 filed Mar. 13, 2013, entitled METHOD FOR THE PURIFICATION OF LECITHIN, which applications are hereby incorporated by reference herein in their entirety.

FIELD OF THE INVENTION

The present invention relates to a method for the purification of lecithin, purified lecithin, and food products comprising the purified lecithin.

BACKGROUND OF THE INVENTION

Lecithin may become contaminated with e.g. poly-aromatic hydrocarbons (PAH's), pesticides and other contaminants during its extraction process from oil seeds. Some of these contaminants, and especially PAH's, can be carcinogenic and pose a problem when the lecithin is to be used in food and animal feed, and especially in infant food products.

Methods for removing PAHs from liquids have been described in the art. For example, U.S. Pat. No. 6,270,676 describes a process for removing ethers and/or polycyclic aromatic hydrocarbons from water. The process requires adsorbing the contaminants on an adsorber resin of divinyl benzene/styrene copolymer, then desorbing the adsorbed contaminants with steam and finally regenerating the adsorber resin. The methods of the prior art are however not directly applicable to lecithin. This is because lecithin is too viscous. As such, putting the lecithin through a packed column or a filter is very difficult.

It is thus an object of the present invention to provide a method for the purification of lecithin that is capable of effectively and economically removing contaminants such as PAH's.

SUMMARY OF THE INVENTION

In a first aspect, the present invention relates to a method for the purification of lecithin. The method comprises the steps of:
a. reducing the viscosity of lecithin to a viscosity of less than about 10 Pa·s; then
b. mixing the lecithin with granulated active carbon; then
c. separating the lecithin from the granulated active carbon and recover purified lecithin.

In a second aspect, the present invention relates to lecithin which is substantially free of poly-aromatic hydrocarbons, and preferably also substantially free of pesticides, organic solvents or particulates.

In a third aspect, the present invention relates to a food or feed product comprising the purified lecithin. The food product is preferably infant food product.

DETAILED DESCRIPTION

The present invention relates to a method for the purification of lecithin.

Lecithin includes a family of polar lipids, including phospholipids. Typically phospholipids are found in cell membrane structures and have a tendency to aggregate into structures, such as, for example, lamellar, hexagonal structures. A phospholipid or phosphatide is a molecule that is similar to a triglyceride, except that the sn3 position has a phosphate group and a functional group attached, rather than a third fatty acyl chain. Major phosphatides existing in plant oils include, for example, phosphatidyl choline (PC), phosphatidyl ethanolamine (PE), phospatidyl serine, phosphatidyl glycerol, phosphatidyl inositol (PI), and phosphatidyl acid (PA). Lecithin also contains non-phosphatide components including, for example, triglycerides, sterols, tocopherols, and carbohydrates.

Lecithin may be a by-product of vegetable oil production processes. Lecithin is typically produced after the extraction and before the oil-refining process. Because it is a by-product, the quality of the lecithin may vary a lot depending, in part, on the quality and type of seeds from which the oils are produced. Lecithin may be produced from any vegetable oil, including, but not limited to, soybean oil, sunflower oil, corn oil, cottonseed oil, palm oil and rapeseed oil. Lecithin also may be of animal origin, such as, for example, fish or eggs. Commercially available lecithins may be derived from soybeans, rapeseed, and sunflower seeds, and are available both in liquid form (e.g. dissolved in soybean or other edible oil) or in dry powdered form. Many lecithins are obtained from vegetable oil by mixing vegetable oil with water, which hydrates the lecithin and renders it substantially insoluble in the vegetable oil, thereby permitting centrifugal separation of the hydrated lecithin (gums) from the oil. The separated gums may be dried to provide a lecithin and redissolved in a suitable edible oil to provide a lecithin with a desired viscosity. Preferred lecithin as used in the process of the present invention is lecithin in liquid form.

In some embodiments, the lecithin can be a modified lecithin. Examples of a modified lecithin include, but are not limited to, hydrolyzed lecithin, acetylated lecithin and hydroxylated lecithin. Lecithin contains functional groups (e.g., double bonds) that make it reactive in a number of chemical reactions. As used herein the term "modified lecithin" refers to lecithin molecules that have been modified by reaction of one or more of the functional groups (e.g., double bonds) of the phosphatides with one or more reagents or enzymes that modify the chemical composition of the phosphatides.

In some embodiments, the lecithin is a PC rich lecithin. In some embodiments, the PC rich lecithin is PC enriched, which means the lecithin has undergone a fractionation process and is PC fractionated. A typical method to fractionate lecithin is by adding alcohol to the lecithin in order to separate the lecithin into a PC rich fraction and a PC poor fraction. A PC rich lecithin formed by this process would be an alcohol fractionated PC enriched lecithin. In some embodiments, the PC rich lecithin is a lecithin containing a certain amount of phosphatidyl choline (PC), but the lecithin is not fractionated. In some embodiments, a PC concentration of the PC rich lecithin is at least about 30 wt %. As described in further detail below, the PC concentration of lecithin is based on the acetone insoluble fraction of lecithin. It is recognized that PC rich lecithin may be formed by other known methods, such as, for example, adjusting pH.

Lecithin may be characterized by the amount of phosphatides in the lecithin, which may be determined by the "acetone insolubility (AI)" method defined in American Oil Chemists' Society (AOCS) Method Ja 4-46. As such, all types of lecithin may be expressed in terms of a percentage of acetone insolubles. For example, standard soy-based lecithin typically contains about 62 to 64 wt % AI; plastic soy lecithin typically contains a minimum of about 65 wt % to 69 wt % AI. A soy bean lecithin with an AI of 62% consists typically of 12-18% PC, 10-15% PE, 8-11% PI, 3-8% PA, 5-7% glycolipids, 2-3% sterols, 5% carbohydrates, 36% of triglycerides, and 1% of moisture. The AI fraction is the same as the polar fraction of the lecithin, and contains the phospholipids, glycolipids and sterols and carbohydrates.

In some embodiments, the percentage of acetone insolubles in the lecithin composition is between about 50 wt % and about 98 wt %. Typically, modified lecithin has an acetone insolubility of about 50 wt % or greater, for example, about 52 wt % or greater, about 54 wt % or greater, about 56 wt % or greater, about 58 wt % or greater, or about 60 wt % or greater. In some embodiments having PC rich lecithin, the PC concentration is at least about 30 wt % of the total amount of acetone insolubles; in other embodiments the PC concentration is at least about 40 wt % of the total amount of acetone insolubles; at least about 50 wt % of the total amount of acetone insolubles; at least about 60 wt % of the total amount of acetone insolubles; and at least about 70 wt % of the total amount of acetone insolubles.

The first step of the process of the present invention comprises reducing the viscosity of the lecithin to less than 10 Pa·s, preferably to less than 8 Pa·s, even more preferably to less than 6 Pa·s. Most preferably, the viscosity of the lecithin is reduced to from 40 Pa·s to 2 Pa·s.

In one embodiment, the viscosity of the lecithin is reduced by increasing its temperature. Preferably, the viscosity of the lecithin is reduced by increasing the temperature to a temperature from about 20° C. to about 95° C., preferably to a temperature of from about 20° C. to about 80° C., and more preferably to a temperature from about 50° C. to about 60° C.

In another embodiment, the viscosity of the lecithin is reduced by mixing the lecithin with a vegetable oil at a temperature of from about 10° C. to about 90° C. , preferably from about 15° C. to about 60° C. , more preferably from about 20° C. to about 30° C., most preferably at about room temperature. The vegetable oil may be any type of vegetable oil, including, but not limited to olive oil, rapeseed oil, sunflower oil, palm oil, corn oil, rice bran oil, ground peanut oil, soybean oil, and blends thereof. The vegetable oil may be a cold pressed or a refined oil. The vegetable oil may be modified. An example of a modified oil includes, but is not limited to, an interesterified oil.

In yet another embodiment, the viscosity of the lecithin is reduced by mixing the lecithin with an organic solvent. Preferred organic solvents are hexane, ethanol and toluene. The most preferred organic solvent is hexane. The lecithin can be mixed with the organic solvent at a temperature of from about 5° C. to below the boiling point of the organic solvent, preferably at a temperature from about 20° C. to about 30° C., and more preferably at about room temperature.

After reducing the viscosity, the lecithin is then mixed with granulated active carbon in order to absorb contaminants thereon. Preferably, about 90 wt % of the granulated active carbon has a diameter of from about 0.2 mm to about 4 mm, preferably from about 0.3 mm to about 3 mm, even more preferably from about 0.4 mm to about 2 mm.

Preferably, the lecithin is mixed with the granulated active carbon at a ratio of from about 0.05% to about 3% by weight of granulated active carbon to lecithin, preferably at a ratio of from about 0.05% to about 2% by weight, even more preferably from about 0.1% to about 1.5% by weight of granulated active carbon to lecithin.

The granulated active carbon should be mixed such that it is efficiently spread throughout the lecithin for a sufficient period of time so that the contaminants can come in contact with the granulated active carbon and be adsorbed thereto. The mixing conditions should be such that the granulated active carbon is preferably uniformly dispersed throughout the lecithin and that it remains in dispersion (not sedimenting). The mixing conditions should also prevent that the granulated active carbon is ground, as then it will be very difficult to remove the active carbon later on. Typically, the mixing time ranges from about 1 hour to about 100 hours, preferably from about 12 hours to about 72 hours, more preferably about 24 hours. A uniform dispersion can be obtained by mixing for example with a paddle stirrer at 100 rpm.

Once the contaminants are adsorbed on the granulated active carbon, the lecithin and granulated active carbon are then separated in order to recover purified lecithin. Preferably, gravitational forces are used for the separation process. Suitable devices for separation include decanters e.g. GEA Westfalia Model CA 225 (Oelde, Germany) and centrifuges e.g. GEA Westfalia Model SC 6 (Oelde, Germany), a decanter being preferred.

Optionally, the recovered lecithin may further be filtrated.

The lecithin recovered from the process of the present invention is purified, and preferably substantially free of contaminants. In particular, the purified lecithin is substantially free of PAH's. With substantially free, it is meant that the lecithin contains less than about 10 µg/kg wet weight of PAH4. With PAH4, it is meant the combination of the following chemicals: benzo(a)pyrene, benzo(a)anthacene, benzo(b)fluoranthene and chrysene. With the process of the present invention, it is further possible to obtain purified lecithin having a PAH4 content of less than about 1.0 µg/kg wet weight, preferably even less than about 0.5 µg/kg wet weight, more preferably even less than about 0.3 µg/kg wet weight.

The level of benzo(a)pyrene in the purified lecithin is preferably less than about 2 µg/kg wet weight, more preferably less than about 1 µg/kg wet weight, and even more preferably less than about 0.05 µg/kg wet weight.

The process of the present invention is also capable of removing contaminants beyond PAH's, such as pestcicides. As such, the purified lecithin is preferably also substantially free of pesticides.

Lecithin may further contain small particulates which desirably should be removed as well. The removal of particulates from lecithin is preferably carried out after the recovery of the purified lecithin according to the process of the present invention, to ensure that any residues from the granulated active carbon are removed. The process for removing particulates comprises the steps of reducing the viscosity of the recovered purified lecithin to less than about 1.5 Pa·s, preferably to less than about 1.0 Pa·s, by mixing the lecithin with an organic solvent. Preferred solvents are hexane or ethanol, with hexane being most preferred. Preferably, the amount of organic solvent in the mixture in case ethanol is used, does not exceed about 33 wt % of the mixture, and preferably is between about 20-25 wt % of the mixture. In case hexane is used the amount of organic solvent should not exceed about 99 wt %, and preferably be about 60 to 80 wt % of the mixture. Then, residual particles or contaminants are removed from the lecithin by means of gravitational forces. Suitable devices for separation include decanters and centrifuges. A preferred centrifuge is a clarifier centrifuge e.g SC 6 from GEA Westfalia (Oelde, Germany). Finally, the solvent is removed for example by evaporation, and lecithin is recovered.

Alternatively, the removal of particulates may be carried out before step a) of the process of the present invention.

Preferably, the process for removing PAH's and the process for removing particulates are sequentially combined in one overall process. The recovered lecithin is thus preferably also substantially free of organic solvent, and preferably also substantially free of particulates. With substantially free of organic solvent, it is meant that the level of organic solvent in the lecithin is less than about 5000 ppm, preferably less than about 3000 ppm, if ethanol is used as solvent, and less than about 10 ppm, preferably less than about 1 ppm, if hexane is used. Preferably the resulting lecithin shows a turbidity (1 wt % lecithin in hexane) of less than about 100 nephelometric turbidity units (NTU). In a highly preferred embodiment, the recovered lecithin is transparent which means that 1 wt % lecithin in hexane shows a turbidity of less than about 10 NTU. The NTU value of lecithin can be measured for example with a Hach® Ratio Turbidimeter 18900 or 2100. 1 g (+/−0.01) of lecithin is added to a glass beaker, and hexane is added up to 100 ml. Then mix the solution well. A measuring tube is filled with the mixture and inserted into the turbiditymeter. The result, expressed in NTU, can be read from the device. However, the process for removing particulates may also be carried out independently. As such, in one embodiment, the process for removing particulates from lecithin comprises the steps of reducing the viscosity of lecithin to less than 1.5 Pa·s, preferably less than 1.0 Pa·s, by mixing the lecithin with an organic solvent. Preferred solvents are hexane, ethanol or toluene, with hexane being the preferred solvent. Then, residual particles or contaminants are removed from the lecithin by means of gravitational forces. Suitable devices for separation include decanters and centrifuges. A preferred centrifuge is a clarifier centrifuge. Finally, the solvent is removed for example by evaporation, and lecithin substantially free of particulates is recovered.

In one embodiment, the present invention relates to food and feed products comprising the purified lecithin. In a highly preferred embodiment, the present invention relates to an infant food product comprising the purified lecithin.

EXAMPLES

Example 1

Liquid sunflower lecithin with an AI content of 63% and contaminated with 6.3 µg/kg benzo(a)pyrene and in total 27 ppb of heavy PAH is fed into a stirred jacketed tank and heated to 50° C. (+/−5° C.).

1.0% by weight of granulated active carbon (Norit GAC 1240) is mixed with the lecithin. After 20 hours of stirring at 100 rpm, the liquid lecithin/granulated active carbon mixture is pumped to a decanter type CA 225-00-33 (GEA Westfalia, Oelde Germany). In the decanter running at a speed of 5400 rpm, the lecithin was separated from the granulated active carbon. The resulting lecithin was collected and analysed again for PAH.

The concentration of benzo(a)pyrene was below the detection limit (<0.5 µg/kg). Also all other heavy PAH were below the detection limit.

Example 2

Liquid Sunflower lecithin with an AI content of 63% and contaminated with 6.3 µg/kg benzo(a)pyrene and in total 27 ppb of heavy PAH is fed into a stirred jacketed tank and heated to 50° C. (+/−5° C.).

1.0% by weight of granulated active carbon (Norit GAC 1240) is mixed with the lecithin. After 20 hours of stirring with 100 rpm the liquid lecithin/granulated active carbon mixture is pumped to a decanter type SC 6-06-576 (GEA Westfalia, Oelde Germany). In the decanter running at a speed of 12000 rpm the lecithin was separated from the granulated active carbon. The resulting lecithin was collected and analysed again for PAH.

The concentration of benzo(a)pyrene was below the detection limit (<0.5 µg/kg). Also all other heavy PAH were below the detection limit.

Example 3

40% liquid sunflower lecithin by weight (hexane insoluble content 1.44 wt %) is mixed with 60% hexane. The mixture had a viscosity at 10° C. of 6 mPa·s. This mixture is fed at a rate of 750 liter/hour and a temperature of 24° C. through a centrifuge type SC 6 (GEA Westfalia, Oelde Germany). The solvent of the light phase is subsequently removed and the resulting lecithin had a residual hexane insoluble content of 0.001 wt %.

Example 4

20% liquid sunflower lecithin by weight (hexane insoluble content 1.44 wt %) is mixed with 80% hexane. The mixture had a viscosity at 10° C. of 3 mPa·s. This mixture is fed at a rate of 375 liter/hour and a temperature of 9° C. through a centrifuge type SC 6 (GEA Westfalia, Oelde Germany). The solvent of the light phase is subsequently removed and the resulting lecithin had a residual hexane insoluble content of 0.006 wt %.

What is claimed is:

1. A method for the purification of lecithin, comprising the steps of:
   a. reducing the viscosity of lecithin to a viscosity of less than about 10 Pa·s; then
   b. mixing the lecithin with granulated active carbon; then
   c. separating the lecithin from the granulated active carbon and recover purified lecithin.

2. A method according to claim 1, wherein the viscosity of lecithin is reduced to from about 40 Pa·s to about 2 Pa·s.

3. A method according to claim 1, wherein the viscosity of lecithin is reduced by increasing the temperature to about 20° C.-95° C.

4. A method according to claim 1, wherein the viscosity of lecithin is reduced by mixing the lecithin with a vegetable oil at a temperature of from about 10° C. to about 90° C.

5. A method according to claim 1, wherein the viscosity of lecithin is reduced by mixing with an organic solvent.

6. A method according to claim 1, wherein 90 wt % of said granulated active carbon has a diameter of from about 0.2 mm to about 4 mm.

7. A method according to claim 1, wherein the lecithin and granulated active carbon are mixed at a ratio of from about 0.05% to about 3% by weight of granulated active carbon to lecithin.

8. A method according to claim 1, wherein the lecithin is separated from the granulated active carbon through gravitational forces.

9. A method according to claim 1, wherein the lecithin is separated from the granulated active carbon by means of a decanter or a centrifuge.

10. A method according to claim 1, further comprising the step of:
   d. filtrating the recovered lecithin.

11. A method according to any claim 1, further comprising the steps of:
- reducing the viscosity of the recovered purified lecithin to less than about 1.5 Pa·s by mixing the lecithin with an organic solvent; then
- removing residual particles or contaminants from the lecithin by means of gravitational forces; then
- removing the solvent from the lecithin and recovering the lecithin.

12. A method according to claim 1, further comprising the steps, before step a of claim 1, of:
- i. reducing the viscosity of lecithin to less than about 1.5 Pa·s by mixing the lecithin with an organic solvent; then
- ii. removing particles or contaminants from the lecithin by means of gravitational forces; then
- iii. removing the solvent from the lecithin and recover the lecithin.

\* \* \* \* \*

UNITED STATES PATENT AND TRADEMARK OFFICE
CERTIFICATE OF CORRECTION

PATENT NO. : 9,328,314 B2
APPLICATION NO. : 14/652900
DATED : May 3, 2016
INVENTOR(S) : Bassam Farid Jirjis et al.

It is certified that error appears in the above-identified patent and that said Letters Patent is hereby corrected as shown below:

Specification

In column 6, line 2, delete "stining" and insert -- stirring --, therefor.

Claims

In column 7, line 1, in claim 11, delete "any".

Signed and Sealed this
Twenty-third Day of August, 2016

Michelle K. Lee
*Director of the United States Patent and Trademark Office*